United States Patent [19]

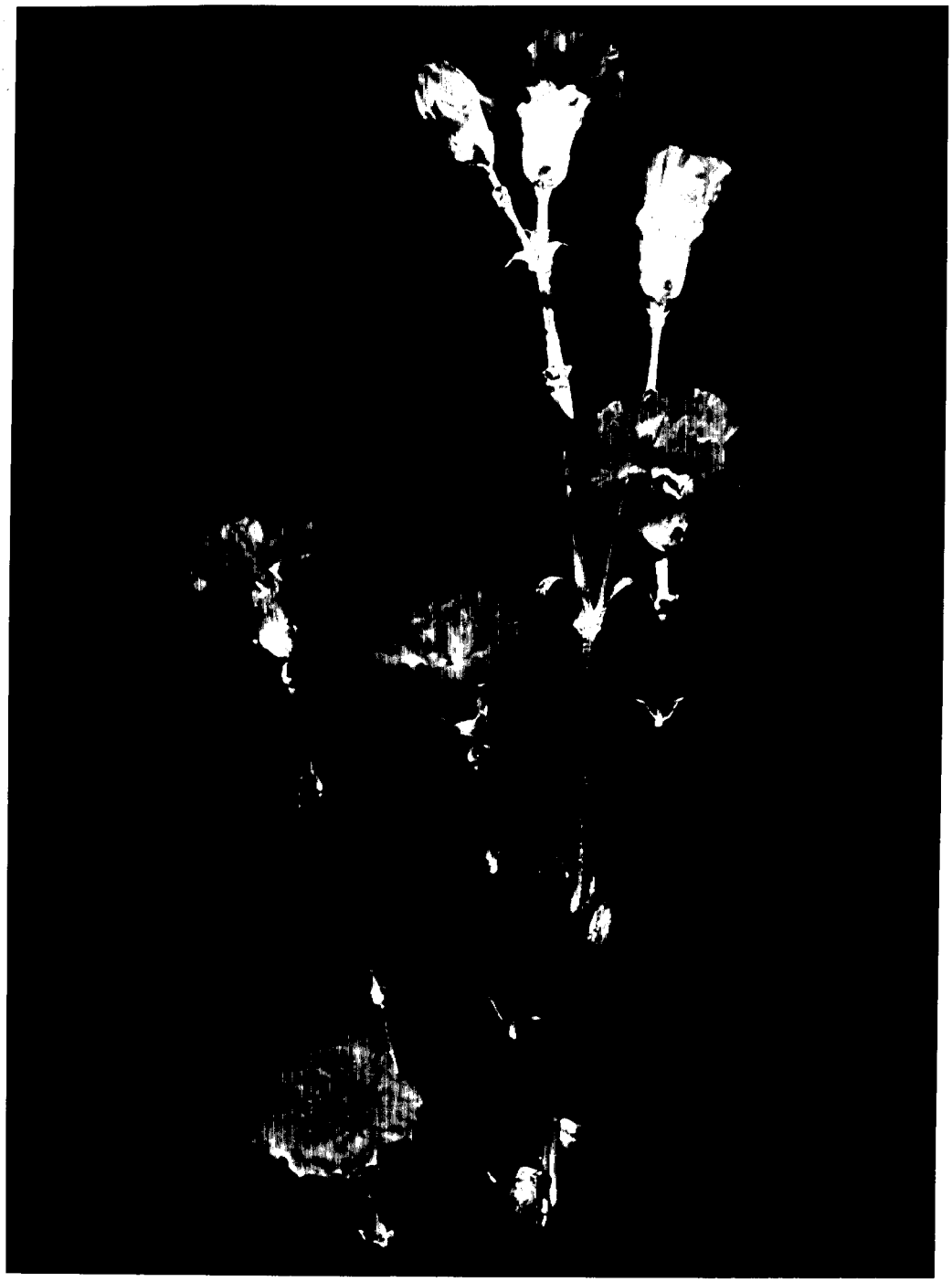

Barberet et al.

[11] Patent Number: Plant 5,793

[45] Date of Patent: Oct. 21, 1986

[54] CARNATION NAMED LONSIMOX

[75] Inventors: Nicole Barberet; Yves Ducloux, both of Antibes, France

[73] Assignee: Laboratoire de Physiologie Vegetale de la Londe, La Londe, France

[21] Appl. No.: 669,938

[22] Filed: Nov. 8, 1984

[51] Int. Cl.[4] ..... A01H 5/00

[52] U.S. Cl. ..... Plt./82

[58] Field of Search ..... Plt./82

*Primary Examiner*—Robert E. Bagwill

*Attorney, Agent, or Firm*—Charles W. Rummler; John R. Lungmus

[57] ABSTRACT

A new and distinct spray carnation cultivar characterized by its profuse production of small flowers of a bright cyclamen red coloration borne in relatively large numbers on each flowering stem, which is of medium height, erect and rigid, the plant having a vigorous growth habit with moderately abundant foliage.

1 Drawing Figure

BACKGROUND OF THE NEW PLANT

Our new carnation variety is the result of our breeding efforts carried on at La Londe-les-Maures-Var-France, with the object of producing a new spray carnation having flowers of a nice color and good quality borne on a plant having a vigorous and upright growth habit and excellent flower production. Our new plant originated as a seedling produced by crossing of selected individually identified carnations growing among our collection of distinctive plants maintained at La Londe for breeding purposes and this particular seedling was selected by us for propagation and test because of its bright red solid color and apparent profuse production of buds and flowers. This new plant was asexually reproduced under our direction, at La Londe, by means of cuttings; and successive propagation through several generations, by both cuttings and in vitro propagation, has demonstrated that the novel characteristics of this plant hold true from generation to generation and appear to be firmly fixed.

DESCRIPTION OF THE DRAWING

Our new carnation cultivar is illustrated by the accompanying photographic drawing which shows, in full color, a typical arrangement of buds and flowers in various stages of opening borne on a single flowering stem, the colors shown being as nearly true to those specified herein as is reasonably possible to obtain by conventional photographic procedures.

DESCRIPTION OF THE NEW PLANT

The following is a detailed description of our new carnation cultivar based upon observations of greenhouse grown plants at La Londe, France, the data having been collected in the spring of 1984. The color designations are specified according to The R.H.S. Colour Chart published by The Royal Horticultural Society of London, England.

THE PLANT

Origin: Seedling.

Parentage:

*Seed parent.*—Stock Plant No. 71 MR 1.

*Pollen parent.*—Stock Plant No. 73 MP 3. These parent plants are unnamed and unpatented varieties which are individually identified in our permanent records and are maintained in our collection of carnation plants at Laboratoire de Physiologie Vegetale de la Londe, to provide stock for breeding purposes.

Classification:

*Botanic.—Dianthus caryophyllus L.*

*Commercial.*—Spray carnation.

Form: Tall, erect bush with at least four stems being emitted near the ground.

Plant height: About 90 cm. in average at 8 months.

Flowering stem:

*Length.*—About 55 cm.

Branching character: The plant has a normal branching habit.

Growth habit: Vigorous and upright with rather rigid stems.

Foliage:

*Quantity.*—Moderately abundant.

*Number of leaves.*—At least 120.

*Leaf size.*—In average, about 9.4 cm. in length and 0.7 cm. in width.

*Shape of leaf.*—Linear with straight margins at the seventh node.

*Texture.*—Leathery.

*Color.*—Both upper and under sides, 189A and B.

*Ribs and veins.*—Hardly noticeable.

*Rachis.*—Hardly noticeable.

THE BUD

Form: Long columnar.

Size:

*Diameter.—About* 1.3 cm. in average.

*Length.*—About 2.8 cm. in average.

Opening rate: Normal.

Color of petals:

*When sepals first divide and as the petals begin to unfurl.*—Bright Red 57B.

Sepals:

*Number.*—Five. The sepals are joined at the lower part and are of acute character at the upper part, being sharp pointed at the apex. The sepals are hooded over the bud and as the flower opens the sepals continue to stand up.

*Color.*—Inside — 145D. Outside — 138A and 144C.

Calyx:

*Shape.*—Cylindrical.

*Size.*—Large. About 1.2 cm. wide in average and about 2.9 cm. long in average.
*Splitting.*—The calyx does not split.
*Aspect.*—Smooth.

Flower Stem:
*Length.*—About 55 cm.
*Character.*—Erect and rigid.
*Color.*—189A and B.

THE FLOWER

Blooming habit: Recurrent and profuse during the mid-season of spring and fall with a tendency to give few blooms in fall.

Size of bloom: Small.
*Diameter.*—About 5.2 cm.
*Depth.*—About 4.5 cm.

Borne: As a simple raceme on single stems of various lengths branching from the main stem.

Shape:
*When bloom first opens.*—High centered.
*As bloom matures.*—Dome shape.

Petalage:
*Number of petals.*—Average about 34.
*Arrangement.*—Imbricated.
*Form.*—Fan-shaped with rounded edges and finely serrated apex.
*Texture.*—Soft.
*Appearance.*—Satiny.
*Color.*—Both outer and inside petals: Upper Side: Body — 57B. Base — Greenish-white. Reverse side — 57C with greenish-white base.

Petaloids: Very rare.
*Size.*—Smaller than petals.
*Color.*—Same as petals.

Flower stem: About 55 cm. in average.
*Character.*—Upright and of very good strength.
*Color.*—199A and B.

Fragrance: A fragrance is present.

Persistence: The flowers hang on and dry.

Lasting quality:
*As cut flowers.*—At least ten days in vase keeping.

Disease resistance: Tolerant to *Fusarium oxysporum* as observed INRA-Antibes-06-France.

REPRODUCTIVE ORGANS

Stamens:
*Number.*—8 to 16.
*Arrangement.*—Around the ovary.
*Anthers.*—Size: Less than 4 mm. Color: Whitish.
*Filaments.*—Length: 2.4 cm. in average. Color: Pinkish white.

Pistils:
*Number.*—Two, exceptionally three.
Styles.—Color: White.
*Stigma.*—Color: Very light pinkish white.

Character of ovaries: Lightly ribbed.

This new spray carnation cultivar appears to be an entirely original variety in respect of its cyclamen red color in the R.H.S. Red Purple Group, sometimes called Rose Bengal.

The expression of the above characteristics can be more-or-less strongly modulated under the influence of the environment conditions, i.e., ground, method of cultivation, latitude, etc. These data are based upon observations made in the spring in the southern part of France.

We claim:

1. A new spray carnation cultivar, substantially as herein shown and described, characterized by the cyclamen red color of its medium sized flowers which are produced profusely during each of the recurrent blooming seasons; and by its vigorous growth habit which is resistant to *Fusarium oxysporum.*

* * * * *